US008765174B2

(12) United States Patent
Hassan et al.

(10) Patent No.: US 8,765,174 B2
(45) Date of Patent: Jul. 1, 2014

(54) CHEWABLE SOFT CAPSULE

(75) Inventors: EmadEldin M. Hassan, Greensboro, NC (US); Warren W. Kindt, Greensboro, NC (US); Roger E. Gordon, Greensboro, NC (US)

(73) Assignee: Banner Pharmacaps Inc., High Point, NC (US)

( * ) Notice: Subject to any disclaimer, the term of this patent is extended or adjusted under 35 U.S.C. 154(b) by 344 days.

(21) Appl. No.: 13/327,293

(22) Filed: Dec. 15, 2011

(65) Prior Publication Data

US 2012/0091605 A1    Apr. 19, 2012

Related U.S. Application Data

(62) Division of application No. 10/512,318, filed as application No. PCT/US03/12983 on Apr. 24, 2003, now Pat. No. 8,097,279.

(60) Provisional application No. 60/375,479, filed on Apr. 25, 2002.

(51) Int. Cl.
    *A61K 9/48*    (2006.01)

(52) U.S. Cl.
    USPC ............ 424/456; 424/441; 424/460; 424/461

(58) Field of Classification Search
    USPC .......................................... 424/465–490, 441
    See application file for complete search history.

(56) References Cited

U.S. PATENT DOCUMENTS

| | | | |
|---|---|---|---|
| 730,826 A | 6/1903 | Kobayashi |
| 1,061,111 A | 5/1913 | Olsson |
| 2,349,430 A | 5/1944 | Hiatt et al. |
| 2,580,683 A | 1/1952 | Kreuger |
| 2,851,364 A | 9/1958 | Peebles |
| 2,853,421 A | 9/1958 | Adams |
| 3,057,723 A | 10/1962 | Jeffreys et al. |
| 3,126,321 A | 3/1964 | Kurtz |
| 3,138,532 A | 6/1964 | Aiello et al. |
| 3,228,789 A | 1/1966 | Glassman |
| 3,427,378 A | 2/1969 | Henderson et al. |
| 3,515,781 A | 6/1970 | Steinberg |
| 3,765,917 A | 10/1973 | Hijiya et al. |
| 3,784,684 A | 1/1974 | Bossert et al. |
| 3,851,051 A | 11/1974 | Miskel et al. |
| 3,865,603 A | 2/1975 | Szymanski et al. |
| 4,083,973 A | 4/1978 | van der Vies |
| 4,187,119 A | 2/1980 | Battard et al. |
| 4,198,391 A | 4/1980 | Grainger |
| 4,279,931 A | 7/1981 | Verwaerde et al. |
| 4,346,116 A | 8/1982 | Verwaerde et al. |
| 4,374,146 A | 2/1983 | Phillips |
| 4,428,927 A | 1/1984 | Ebert et al. |
| 4,450,179 A | 5/1984 | Vink et al. |
| 4,486,412 A | 12/1984 | Shah et al. |
| 4,532,126 A | 7/1985 | Ebert et al. |
| 4,595,583 A | 6/1986 | Eckenhoff et al. |
| 4,673,438 A | 6/1987 | Wittwer et al. |
| 4,701,327 A | 10/1987 | Henmi et al. |
| 4,708,834 A | 11/1987 | Cohen et al. |
| 4,719,112 A | 1/1988 | Mayor et al. |
| 4,734,284 A | 3/1988 | Terada et al. |
| 4,744,988 A | 5/1988 | Brox |
| 4,778,676 A | 10/1988 | Yang et al. |
| 4,795,642 A | 1/1989 | Cohen et al. |
| 4,804,542 A | 2/1989 | Fischer et al. |
| 4,849,023 A | 7/1989 | Devos et al. |
| 4,888,239 A | 12/1989 | Brox |
| 4,935,243 A | 6/1990 | Borkan et al. |
| 4,950,689 A | 8/1990 | Yang et al. |
| 5,225,197 A | 7/1993 | Bolt et al. |
| 5,236,719 A | 8/1993 | Meyers et al. |
| 5,324,751 A | 6/1994 | DuRoss |
| 5,360,615 A | 11/1994 | Yu et al. |
| 5,376,688 A | 12/1994 | Morton et al. |
| 5,468,728 A | 11/1995 | Sawai et al. |
| 5,496,558 A | 3/1996 | Napolitano et al. |
| 5,637,313 A | 6/1997 | Chan et al. |
| 5,753,255 A | 5/1998 | Chavkin et al. |
| 5,760,094 A | 6/1998 | Alexander et al. |
| 5,780,056 A | 7/1998 | Akamatsu et al. |

(Continued)

FOREIGN PATENT DOCUMENTS

| | | | |
|---|---|---|---|
| EP | 0 121 321 A1 | 10/1984 |
| EP | 0 161 915 A1 | 11/1985 |

(Continued)

OTHER PUBLICATIONS

Burger, W.H., "Gelatine," *Hunnius Pharmazeutisches Worterbuch*, Walter de Gruyter, Berlin, 593-594 (1993).

(Continued)

*Primary Examiner* — Michael G Hartley
*Assistant Examiner* — Micah-Paul Young
(74) *Attorney, Agent, or Firm* — Womble Carlyle Sandridge & Rice, LLP

(57) ABSTRACT

A matrix formulation for a soft chewable capsule is provided which includes a gel-forming composition, a plasticizer, a polymer modifier, and water. The polymer modifier may be a carboxylic acid or other organic compound that alters the physical and/or chemical properties of the capsule formulation. A chewable soft capsule is also provided, having enhanced organo-leptic and processing properties. An active material may be delivered to a user using this dosage form. A method of forming the chewable soft capsule is also provided.

21 Claims, No Drawings

(56) References Cited

U.S. PATENT DOCUMENTS

| | | | |
|---|---|---|---|
| 5,837,277 | A | 11/1998 | Hayward |
| 5,928,664 | A | 7/1999 | Yang et al. |
| 5,948,388 | A | 9/1999 | Steele et al. |
| 5,955,098 | A | 9/1999 | Dugger, III |
| 6,020,003 | A | 2/2000 | Stroh et al. |
| 6,027,746 | A | 2/2000 | Lech |
| 6,060,078 | A | 5/2000 | Lee |
| 6,110,486 | A | 8/2000 | Dugger, III |
| 6,132,442 | A | 10/2000 | Ferragamo et al. |
| 6,251,426 | B1 * | 6/2001 | Gullapalli ............ 424/451 |
| 6,258,380 | B1 | 7/2001 | Overholt |
| 6,287,596 | B1 | 9/2001 | Murakami et al. |
| 6,322,806 | B1 | 11/2001 | Ream et al. |
| 6,322,828 | B1 | 11/2001 | Athanikar et al. |
| 6,432,442 | B1 | 8/2002 | Buehler et al. |
| 6,589,551 | B1 | 7/2003 | Jolliffe |
| 6,790,495 | B1 | 9/2004 | Tomka et al. |
| 2004/0076664 | A1 | 4/2004 | Bonura |
| 2005/0136104 | A1 | 6/2005 | Rowe et al. |
| 2007/0292501 | A1 | 12/2007 | Udell |

FOREIGN PATENT DOCUMENTS

| | | |
|---|---|---|
| EP | 0 243 930 A1 | 4/1987 |
| EP | 0 374 359 A1 | 6/1990 |
| EP | 1 127 914 A2 | 8/2001 |
| EP | 1 103 254 A1 | 3/2005 |
| FR | 2 535 608 A1 | 5/1984 |
| FR | 2 535 608 B1 * | 5/1984 |
| GB | 610538 | 10/1948 |
| JP | 56089833 | 7/1981 |
| JP | 84044096 | 10/1984 |
| JP | 1020078 | 1/1989 |
| JP | 4145017 A | 5/1992 |
| JP | 5238954 A | 9/1993 |
| WO | WO 91/04757 | 4/1991 |

OTHER PUBLICATIONS

Dictionary.com disclosure "Dextrose" Retrieved from internet Oct. 6, 2005.

Dictionary.com disclosure "Grape Sugar" Retrieved from internet Oct. 6, 2005.

GMIA Q&A/FAQ disclosure, 2001, downloaded from world wide web at www.gelatin-gmia.com/html/ganda.html.

J. Stein Carter disclosure "Carbohydrates" copyright 1996.

P.M. Gilsenan, S.B. Ross-Murhpy, Elsevier Science Ltd., "Rheological Characterization of Gelatins from Mammalian and Marine Sources," 191-195 (1999).

JP 4145017 A (Shiseido Co. Ltd.) May 19, 1995 (abstract) [online] Thomson Innovation (2011) Retrieved from Thomson Innovation, pp. 1-2.

JP 5238954 A (Toyo Capsule KK) Sep. 17, 1993 (abstract) [online] Thomson Innovation (2011) Retrieved from Thomson Innovation, pp. 1-2.

* cited by examiner

CHEWABLE SOFT CAPSULE

RELATED APPLICATIONS

The present application is a divisional of U.S. patent application Ser. No. 10/512,318, filed Oct. 22, 2004, which is a national stage application under 35 U.S.C. §371 of International Application Serial No. PCT/US03/12983, filed Apr. 24, 2003, which claims benefit of priority under 35 U.S.C. §119 to U.S. Provisional Patent Application Ser. No. 60/375,479, filed on Apr. 25, 2002, the contents of each are hereby incorporated by reference in their entirety.

TECHNICAL FIELD

The present invention relates generally to a chewable matrix composition. The invention also relates to chewable soft capsules and to a process for their preparation, and in particular to chewable soft capsules having a controllable chewable consistency.

BACKGROUND

Chewable dosage forms are manufactured as solids, such as chewable tablets, or elastic semi-solids such as chewing gums, molded gels, or chewable soft capsules. While elastic semi-solid forms provide better mouth feel and customer acceptance, chewable soft capsules have a further benefit of being totally ingestible and can deliver accurate amounts of active ingredients.

Soft capsules formed of a sheath encapsulating a fill or a matrix are one type of dosage form generally used for administering perorally a medicament, vitamin, nutritional supplement, or other material. Certain types of these soft capsules are designed to be chewed by the user. Chewable soft capsules, or chewable soft gels, are traditionally designed so that the user chews upon the capsule to release the fill into the mouth, instead of swallowing the capsule with the fill still encapsulated within the sheath. Chewable capsules are particularly suitable for administering analgesics, vitamins, minerals and cold remedies. After the fill has been released, the user chews the fractured sheath until it is partially or completely dispersed. Alternatively, the sheath may include a chewing gum base material that is not made for swallowing.

Although chewable soft capsules provide an effective dosage system, user acceptance has been limited by the capsules' organo-leptic properties, which are sometimes criticized as being leathery or rubbery, as well as the difficulty that some users experience in consuming the fractured sheaths after the fills have been released. Current soft capsules share the disadvantage of having a distinguishable difference between the sheath and fill in terms of texture and mouth-feel. In addition, they tend to harden over time. The objective of this invention is to address these issues and limitations.

SUMMARY

The present invention is directed generally to a soft capsule useful as a dosage delivery system. The soft capsule, when used as an oral dosage form, exhibits a consistency, texture and other organo-leptic properties found desirable in a chewable capsule. The capsule, which is suitable for chewing, generally includes a gel-forming polymer, a plasticizer, a polymer modifier, and, water. The capsule also includes an active ingredient that is to be delivered to the user, and optionally contains flavoring agent, sweetener, and/or a taste-masking agent.

In one embodiment, the soft capsule generally includes a matrix encapsulated in a sheath. The matrix is formed of a gel-forming polymer, a first plasticizer, water and a polymer modifier. The sheath is formed of a second gel-forming polymer and a second plasticizer. The active ingredient may be contained within the matrix. One or both of the first and second gel-forming polymers may be a gelatin that exhibits a bloom in a predetermined range.

In one particular embodiment, the matrix includes a gelatin exhibiting a bloom in the range of about 0 to about 250. The sheath includes a gelatin that exhibits a bloom in the range of about 80 to about 250.

In another embodiment, the soft capsule has a matrix formed of a gelatin that exhibits a bloom in the range of about 0 to about 80 and a sheath that exhibits a bloom in the range of about 100 to about 150.

In yet another embodiment, the matrix includes a gelatin exhibiting a bloom in the range from about 20 to about 250.

In yet another embodiment, the matrix includes a gelatin exhibiting a bloom in the range from about 40 to about 80.

The polymer modifier used to form the matrix of the soft capsule of the present invention generally includes a carboxylic acid. In one embodiment, the polymer modifier used to form the matrix of the soft capsule is selected from lactic acid, fumaric acid, tartaric acid, citric acid, glycolic acid, and combinations thereof.

The plasticizer used to form the matrix and/or sheath of the soft capsule may include a polyol. In another particular embodiment, the soft capsule is formed using a plasticizer selected from glycerol, sorbitol, maltitol, xylitol, and combinations thereof.

A method of making a soft capsule is also encompassed by the present invention. The method generally includes the step of combining a gel-forming polymer with a polymer modifier, incubating the combined gel-forming polymer and polymer modifier to form a matrix; and, encapsulating the matrix to form a chewable soft capsule.

In one embodiment, the method of forming a chewable soft capsule for administering an oral dosage of an active ingredient includes the steps of: mixing a gelatin, a plasticizer, a polymer modifier, and water together to form a matrix, incubating the matrix, cooling the matrix, and encapsulating the matrix in a sheath. In this embodiment, the gelatin exhibits a bloom in the range of about 0 to about 250 and the plasticizer includes a polyol. Also, the polymer modifier includes a carboxylic acid and the sheath includes a plasticizer and a gelatin that exhibits a bloom in the range of about 80 to about 250.

These and other embodiments and advantages are contemplated by the present invention, which is set forth in detail below.

DETAILED DESCRIPTION

This invention provides chewable soft gel compositions that minimize or reduce the traditional user's complaints regarding a perceived major difference in texture between the matrix and the capsule shell or sheath that is a result of the current technology. Therefore, this invention describes chewable softgel compositions with homogeneous, controllable mouth-feel for the whole capsule.

The soft gel is made from a hydrophilic matrix comprising a gel-forming polymer and its oligomers or hydrolysates, in presence of a polymer modifier that can control the texture, viscosity, and melting point of the matrix. In addition, the sheath comprises a polymer modifier, along with the gel-forming polymer composition, and plasticizer. Such a combination has the benefit of providing a stable composition where mass transfer between the shell and the matrix is reduced due to the structural similarity between the matrix and the shell.

A soft capsule exhibiting organo-leptic properties that are appropriate for use as a chewable dosage form for delivering therapeutic, diagnostic, and/or dietary agents is set forth herein. The organo-leptic properties of the soft capsule, such as, for example, texture, and chewiness, are enhanced by the polymer modifier included in the capsule formulation. In addition, the polymer modifier enhances the physical and/or chemical properties of the gel-forming polymers that are used to form the capsule matrix and/or sheath, thereby facilitating the processing of the soft capsule. The soft capsules generally include a hydrophilic, watersoluble matrix that includes one or more active ingredients and is encapsulated in hydrophilic, water-soluble sheath. The matrix and the sheath are generally formed of similar materials, although variations in their compositions are contemplated by the present invention.

As used herein, the terms "gel-forming polymer" and "gel-forming composition" refer to any natural or synthetic polymeric material or partial hydrolysate of a polymer that can form a gel when appropriately dissolved or dispersed in water or aqueous media. Examples of gel-forming compositions include proteins such as different types of gelatins from different sources. Specific examples are: acid and lime bone bovine gelatins; pig bone gelatin; skin pig gelatin; skin bovine gelatin; and fish gelatin. Other examples of gel-forming compositions are of polysaccharide nature. Specific examples are: sodium and calcium alginate; natural and modified starch and starch hydrolysates; pectins and amylopectins; and cellulose derivatives, such as hydroxypropyl-methyl cellulose, and carboxymethyl cellulose, and salts thereof. A gel-forming composition can be a hydrophilic polymer, alone or in combination with its building units, its oligomers, or hydrolysate. As used in the present description, the term "active ingredient" is intended to include therapeutic, diagnostic or nutritional agents, such as medicaments, vitamins, minerals, fruit extracts, herbals and other encapsulatable materials that are intended for local effect in the mouth or the gastro-intestinal tract, or for systemic effect, or combinations thereof understood by those skilled in the art to support the desired effect. Examples of active ingredients useful in this application are: anti-asthmatic drugs such as salbutamol, theophylline; anti-epileptic drugs such as phenytoin; analgesics such as paracetamol, naproxen, ibuprofen, aspirin, meloxicam, and celecoxib; nonsteroidal anti-inflammatory drugs (NSAIDs); beta-lactam antibiotics such as amoxycillin; macrolide antibiotics such as azythromycin, and clarythromycin; mineral supplements, such as iron, potassium, calcium, magnesium supplements and salts thereof; and vitamins, such as vitamins C, B complex, A, E, K, and D; and other food supplements.

As used herein, "polymer modifier" refers to a pharmaceutically acceptable compound that has the ability, under the appropriate process conditions, to alter one or more physical and/or chemical properties of one or more of the gel-forming polymers disclosed herein or generally known for use in soft capsule formulations, so as to enhance the performance characteristics of the capsule formulation during processing and/or the performance characteristics and/or physical properties of the finished capsule product.

The polymer modifier of the present invention is included in the soft capsule of the present invention in order to alter one or more physical and/or chemical characteristics of the gel-forming polymers that are contained in the capsule formulations. As an example, the polymer modifier may reduce the melting point of the gel-forming polymer in the matrix formulation. With the melting point reduced, less heat is required to place the gel-forming polymer in a liquid state, thereby reducing the energy cost and time required to process the formulation and allowing the incorporation of heat-sensitive drugs or agents.

In addition to a possible reduction in the melting point of the gel-forming polymer, the polymer modifier may reduce the viscosity of one or more of the gel-forming compositions found in the capsule formulation, thereby providing a formulation that may flow more easily during processing (a "flowable" composition). Again, capsule manufacturing may be facilitated by such an alteration. Gel modifier can also prevent gel hardening upon gel storage and improve the disintegration and dissolution of the chewable products in the mouth.

A third illustrative example of the effect that the polymer modifier may have is a reduction of the molecular weight of one or more gel-forming polymers of the capsule formulation. Such a reduction also tends to affect other physical properties of the gel-forming polymers, both during capsule production and in the finished capsule product. The polymer modifier of the present invention also may enhance the texture or chewiness of the finished soft capsule. The capsule texture may tend to be less "leathery" than it would be in the absence of the polymer modifier, thereby providing a more acceptable mouth feel for the capsule user.

Although these particular examples are set forth herein describing the possible impact the polymer modifier has upon the capsule formulation and the finished capsule product, these examples are provided for the purpose of illustration and not to limit the scope of the present invention. These specific possible effects need not occur in order for a capsule formulation to fall within the scope of the present invention. Indeed, these and/or other effects may be realized by the inclusion of a polymer modifier into a capsule formulation, thereby providing a soft capsule that is acceptable for chewing.

Soft gel capsules generally are produced by a rotary die process as set forth by J. P. Stanley in "The Theory and Practice of Industrial Pharmacy," L. Lachman, (editor), Lea and Febiger (publisher), Philadelphia (1976), which is incorporated by reference as if fully set forth herein. In the process of the invention, a molten mass of a gel-forming polymer, such as, for example, a gelatin formulation, is fed from a reservoir onto drums to form two spaced sheets or ribbons of gelatin in a semi-molten state. These ribbons are fed around rollers and brought together at a convergent angle into the nip of a pair of roller dies that include opposed die cavities. A matrix containing an active ingredient to be encapsulated is fed into the wedge-shaped joinder of the ribbons.

The gelatin ribbons are continuously conveyed between the dies, with portions of the matrix being trapped between the sheets inside the die cavities. The sheets are then pressed together, and severed around each die so that opposed edges of the sheets flow together to form a continuous gelatin sheath around the entrapped medicament. The part of the gelatin sheet that is severed from the segments forming the capsules may then be collected for recycling. The very soft capsules are then dried to increase the integrity of the sheath, and packaged for later distribution and consumption.

The chewable soft capsules of the present invention are generally formed by combining the gel-forming composition, polymer modifier, plasticizer, and water with or without mixing, and while maintaining the heat of the mixture in a range between about 40 and about 75 degrees Celsius. This matrix mixture is then allowed to incubate for about 4 to about 72 hours, while its temperature is maintained in the range of about 40 to about 75 degrees Celsius. The matrix mixture is then cooled to a temperature in the range of about 30 to about 40 degrees Celsius.

The matrix mixture is then encapsulated. The capsules are then air-cooled to a temperature in the range of about 5 to about 25 degrees Celsius. The capsules are also dried to a final water content of a range of about 5 to about 20 percent by weight. Final water content can also be from about 5 to about 10 percent. Prior to drying, the matrix can comprise water from about 20% to about 50% by weight. Prior to drying, water content can also be about 25% to about 35% by weight. Active ingredients can be added from the start of preparing the gel mass, if they are chemically and physically stable. Unstable actives can be added, preferably as a last step before encapsulation to minimize any possibility for degradation. The performance properties of a gel-forming composition are affected in part by its cohesive strength, which, in the case of at least gelatin, is expressed as "bloom." This bloom value is determined by measuring the weight in grams required to move a plunger 0.5 inch in diameter, 4 mm into a 6.67% gelatin gel that has been held for 17 hours at 10° C.

Chewable soft gel capsules are designed to at least partially disperse or dissolve in the user's mouth, upon chewing, within a brief period of time so that the chewable mass can be swallowed. Therefore, in addition to the above properties, the remains of the capsule should tend to be soluble after the active ingredient has been released. These remains should also have a good "mouth feel." As used herein, "mouth feel" describes chewability. Chewing the capsule remains should be a pleasant, or at least not an unpleasant, sensation that results in a swallowable composition.

Surprisingly, it has been found that a chewable soft capsule having these desired characteristics can be produced from a capsule formulation including an appropriate amount of polymer modifier that alters one or more characteristics of the gel-forming composition therein. Such a capsule formulation, examples of which are provided below, has been found to produce chewable soft capsules that exhibit a desirable mouth-feel and solubility.

In one embodiment, the matrix formulation, prior to drying, of the present invention includes the following ingredients in the specified percentages:

TABLE 1

Matrix Formulations

| INGREDIENT | % BY WEIGHT |
| --- | --- |
| Gel-Forming composition | 15-80 |
| Polymer modifier | 0.1-10 |
| Plasticizer | 5-40 |
| Water | 5-30 |
| Active Ingredient | 0.01-70 |
| Other Ingredients, e.g., flavors, sweeteners, and taste-masking known in the industry | 0.01-15 |

The gel-forming polymer of the above embodiment may be a gelatin that exhibits a bloom in the range of about 0 to about 250. The plasticizer may be a polyol, such, for example, glycerol, sorbitol, maltitol, xylitol, or combinations thereof. The polymer modifier may be a mono, di, or poly carboxylic acid. More specifically, the polymer modifier may be lactic acid, fumaric acid, tartaric acid, citric acid, glycolic acid or a combination of two or more of these acids.

In this embodiment, the capsule may also include a sheath formulation (before drying) including the following ingredients in the specific ranges:

TABLE 2

Sheath Formulations

| INGREDIENT | % BY WEIGHT |
| --- | --- |
| Gel-Forming composition | 25-55 |
| Plasticizer | 5-40 |
| Water | 15-40 |
| Other Ingredients, e.g., color, flavor, or sweetener. | 0.1-10 |

As with the matrix formulation, the gel-forming polymer may be a gelatin. The gelatin may exhibit a bloom in the range of about 80 to about 250. The plasticizer of this sheath formulation may be a polyol, such as, for example, a polyol selected from glycerol, sorbitol, maltitol, xylitol, or combinations thereof.

In another embodiment, the matrix formulation includes the following ingredients in the specified ranges, after drying:

TABLE 3

Matrix Formulations

| INGREDIENT | % BY WEIGHT |
| --- | --- |
| Gel-Forming composition | 30-70 |
| Polymer modifier | 0.25-5 |
| Plasticizer | 10-30 |
| Water | 5-15 |
| Active Ingredient | 1-25 |
| Other Ingredients | 0.1-5 |

Again, the matrix formulation may include a gelatin as the gel-forming polymer. In this instance, the gelatin may exhibit a bloom in the range of about 0 to about 80. Likewise, the plasticizer may be a polyol, such as one selected from the list set forth above. Also, the polymer modifier again may be a carboxylic acid, such as one selected from the list above.

In this embodiment, the capsule formulation also may include a sheath that includes the following ingredients in the specified ranges:

TABLE 4

Sheath Formulations, After Drying

| INGREDIENT | % BY WEIGHT |
| --- | --- |
| Gel-Forming composition | 10-70 |
| Plasticizer | 10-30 |
| Water | 5-15 |
| Other Ingredients | 0.1-10 |

The gel-forming polymer of this sheath formulation may be a gelatin, which exhibits a bloom in the range of about 100 to about 175.

It will be understood that different percentages may be selected within the above ranges so that the sum of the percentages of the sheath ingredients is equal to 100%. If additional ingredients are used, the percentages will be adjusted within the ranges listed to accommodate the additional ingredients.

In the case of a capsule formulation including both a matrix and a sheath, the matrix may include a first gel-forming polymer and a first plasticizer and the sheath may include a second gel-forming polymer and a second plasticizer. Depending upon the specific formulation, the first and second gel-forming polymers may be either identical to each other or differ in their chemical compositions, bloom values and/or amounts. Likewise, the first and second plasticizers may be identical or differ in their compositions and/or amounts.

The chewable soft capsule formed from the above mixture, after being dried for storage and subsequent use, is comprised of the following ingredients in the specified parts by weight:

TABLE 5

Capsule Composition, After Drying

| INGREDIENT | % BY WEIGHT |
|---|---|
| First Gel-Forming Polymer | 20-80 |
| Second Gel-Forming Polymer | 5-25 |
| First Plasticizer | 10-40 |
| Second Plasticizer | 1-10 |
| Polymer Modifier | 0.5-10 |
| Active Ingredient | 0.01-70 |
| Other Ingredients | 0.1-15 |
| Water | 5-20 |

EXAMPLES

Examples 1-5

The following examples describe the manufacture and testing of various matrix formulations for acceptable practice.

Gelatin, gelatin hydrolysate, and glycerol were mixed and heated to about 65° C. overnight. Citric acid was then added and masses were molded and dried at 20° C. under low humidity (20-30%) until the total water content reached about 10%. Dried samples were tested for hardness, water content, and other texture analysis. The hardness ranged from about 1 to about 100 gram force, using a texture analyzer fitted with a round ball probe. The following example formulations are provided for purposes of illustration of certain aspects of the present invention and are not intended to limit the scope thereof. The optimum percentages of each ingredient will depend upon the overall formulation contents, and the identity of the individual ingredients. However, evaluation and selection of the most desirable formulation will be well within the skill of practitioners in this area, once they are familiar with the present disclosure. The values provided in Table 1 for each compound represent the parts per weight of that compound, and the corresponding hardness obtained:

TABLE 6

Matrix Compositions for Examples 1-5

| COMPONENT | 1 | 2 | 3 | 4 | 5 |
|---|---|---|---|---|---|
| Gelatin | 5.9 | 10 | 10 | 10 | 0 |
| Complete Gelatin Hydrolysate | 5.9 | 10 | 10 | 10 | 10 |
| Sorbitol | 14.1 | 10 | 20 | 0 | 10 |
| Glycerol | 5.9 | 0 | 10 | 10 | 10 |
| Water | | | | | |
| Citric Acid | 1.4 | 1.0 | 1.0 | 1.0 | 1.0 |
| Hardness(g) by Texture Analyzer | 4 | 103 | 7 | 59 | 1 |

Hardness was measured after drying. The above amounts are in weight ratios. Water was adjusted so that the water % is constant and around 28% of the mass before drying. A complete gel hydrolysate is a hydrolyzed gelatin that has zero bloom (as used herein, the term "hydrolysate" may indicate a partial or complete hydrolysate, as indicated in the context where the term is used).

Example 6

A Soft Chewable Capsule Composition

A soft chewable capsule composition according to the invention can include the following matrix and sheath:

TABLE 7

Capsule Compositions

| MATRIX COMPOSITION | | SHEATH COMPOSITION | |
|---|---|---|---|
| Glycerol | 27.1 | Glycerol | 16.96 |
| gelatin (60-80 bloom) | 9.03 | Sorbitol | 16.96 |
| sorbitol | 9.03 | gelatin (100 bloom) | 39.92 |
| gel hydrolysate | 27.1 | citric acid | 1 |
| citric acid | 1.79 | water | 24.95 |
| sucralose | 0.15 | flavor | 0.2 |
| water (prior to drying) | 25.58 | color | 0.004 |
| flavor | 0.2 | | |
| color | 0.004 | | |

Example 7

Effect of the Polymer Modifier on Matrix Properties

A gel matrix consisting 14.6% gelatin (60-80 bloom), 14.6% glycerin, 14.6% Sorbitol Special™ (SPI Polyols, Inc., New Castle, Del.), 40% water (before drying) and 1.48% citric acid was made by subjecting the mixture to heat at 60° C. for about 2 hours. The cooked matrix had a melting point of 29° C. After 24 hours of incubation, the same matrix had a melting point of 25.3° C. and its viscosity was reduced to 52% of the initial value, as measured by a cone and plate rheometer (TA instruments, Leatherhead, England).

Example 8

Matrix and Sheath Composition and Method of Manufacturing

A matrix composition consisting of:

| Gelatin (60-80 Bloom) | 9.68 |
|---|---|
| Gelatin hydrolysate | 29.05 |
| Citric acid | 1.80 |
| Sucralose | 0.15 |
| Glycerin | 21.28 |
| Water | 25.12 |
| Color and flavor, add to | 100.00 |

Gelatin and gel hydrolysate were dissolved in water in presence of the plasticizer at about 60° C. The polymer modifier was also added to the mass and was allowed to modify the mass structure by incubation at 60° C. for 12 hours. The above matrix formula had water activity of 0.39. After incubation, encapsulation was performed using a rotary die machine, with the following gel sheath composition:

| Gelatin (100 Bloom) | 39.92 |
|---|---|
| Citric acid | 1.00 |
| Sorbitol Special ™ | 19.57 |
| Glycerin | 19.57 |
| Water | 24.95 |
| Color | 0.004 |

Capsules were dried in a tumble drier where cold air was initially used to congeal the capsule mass and keep the shell shape integrated. Drying was then completed using a tunnel dryer. Dried capsules had a 9.8% water content, and firm texture (a hardness peak of 91.9 gram force) as measured using a TA-XT2 texture analyzer (Texture Technologies, Scarsdale, New York) using a standard two bite texture profile analysis with a 0.25 inch diameter probe at room temperature.

Example 9

Matrix and Sheath Composition and Method of Manufacturing

The matrix composition consisted of:

| | |
|---|---|
| Gelatin (60-80 Bloom) | 9.03 |
| Gelatin hydrolysate | 27.09 |
| Citric acid | 1.79 |
| Sucralose | 0.14 |
| Glycerin | 36.18 |
| Water | 25.56 |
| Color and flavor, added to | 100.00 |

Gelatin and gel hydrolysate were dissolved in water in presence of the plasticizer at about 60° C. The polymer modifier was also added to the mass and was allowed to modify the mass structure by incubation at 60° C. for 12 hours. After incubation, encapsulation was performed using a rotary die machine, with the following gel sheath composition:

| | |
|---|---|
| Gelatin (100 Bloom) | 39.92 |
| Citric acid | 1.00 |
| Sorbitol Special ™ | 19.57 |
| Glycerin | 19.57 |
| Water | 24.95 |
| Color | 0.004 |

Capsules were dried in a tumble drier where cold air was initially used to congeal the capsule mass and keep the shell shape integrated. Drying was then completed using a tunnel dryer. Dried capsules had a 10% water content, and softer texture (a hardness peak of 22.7 gram force) as measured using a TA-XT2 texture analyzer using a standard two bite texture profile analysis with a 0.25 inch diameter probe at room temperature.

Example 10

Chewable Soft Capsule Matrix Containing Active Ingredient in Solution

A chewable soft capsule formulation contains 6.25 mg per unit dose of the antihistaminic, diphenhydramine, was manufactured using the methods explained in examples 9 and 10 where the active was incorporated to the fill matrix after the incubation with the polymer modifier.

The matrix consisted of 9% gelatin (60-80 bloom), 26.9% gelatin hydrolysate 26.9% glycerin, 9% Sorbitol Special™, 1.8% citric acid, 24.7% water, and less 1% of sweetener, color, and flavor.

Example 11

Chewable Soft Capsule Matrix Containing Active Ingredient as a Suspension

A chewable soft capsule matrix containing 80 mg per dose of the analgesic antipyretic active, Paracetamol was manufactured using the methods explained in examples 9 and 10 where the active was incorporated to the fill matrix after the incubation with the polymer modifier.

The matrix consisted of 8.1% gelatin (60-80 bloom), 24.4% gelatin hydrolysate 31.8% glycerin, 1.6% citric acid, and 10.8% Paracetamol as coated powder.

Certain modifications and improvements will occur to those skilled in the art upon a reading of the foregoing description. It should be understood that all such modifications and improvements are properly within the scope of the following claims.

What is claimed is:

1. A method for making a chewable soft capsule comprising:
    (i) combining a first gel-forming composition comprising one or more of gelatin, partially hydrolyzed gelatin, hydrolyzed gelatin carbohydrates, carbopolymers, polysaccharides, starch, modified starch, alginates, hydroxylpropylmethyl cellulose, methyl cellulose, or combinations thereof; a plasticizer; and water to form a matrix;
    (ii) incubating the matrix for a sufficient time to form a flowable matrix; and
    (iii) encapsulating the flowable matrix in a sheath comprising a second gel-forming composition comprising one or more of gelatin, partially hydrolyzed gelatin, hydrolyzed gelatin, carbohydrates, carbopolymers, polysaccharides, starch, modified starch, alginates, hydroxylpropylmethyl cellulose, methyl cellulose, or combinations thereof; a plasticizer; and water to form a chewable soft capsule; and
    wherein said method further comprises:
        combining a polymer modifier selected from one or more mono-, di-, or poly-carboxylic acids, or combinations thereof in the first gel-forming composition, in the second gel-forming composition, or in both gel-forming compositions.

2. The method of claim 1, wherein said polymer modifier is selected from the group consisting of lactic acid, fumaric acid, tartaric acid, citric acid, glycolic acid, salts thereof, buffers thereof, and combinations thereof.

3. The method of claim 2, wherein said polymer modifier is citric acid.

4. The method of claim 1, wherein the polymer modifier content of the chewable soft capsule comprises about 0.1% to about 10% by weight.

5. The method of claim 1, wherein the polymer modifier content of the chewable soft capsule comprises about 0.25% to about 5% by weight.

6. The method of claim 1, wherein the first gel-forming composition comprises gelatin exhibiting a bloom in the range of about 20 to about 250.

7. The method of claim 1, wherein the first gel-forming composition comprises gelatin exhibiting a bloom in the range of about 40 to about 80.

8. The method of claim 1, wherein the incubating is for about 4 to about 72 hours.

9. The method of claim 1, wherein the temperature of the combined matrix is maintained in a range of about 40° C. to about 75° C. during the incubating.

10. The method of claim 1, further comprising cooling the matrix prior to encapsulating.

11. The method of claim 1, wherein the water content of the chewable soft capsule comprises about 5% to about 20% by weight.

12. The method of claim 1, wherein the second gel-forming composition comprises gelatin exhibiting a bloom in the range of about 20 to about 250.

13. The method of claim 1, wherein the second gel-forming composition comprises gelatin exhibiting a bloom in the range of about 40 to about 80.

14. The method of claim 1, wherein the first gel-forming composition comprises about 15% to about 80% of the matrix by weight.

15. The method of claim 1, wherein the second gel-forming composition comprises about 10% to about 70% of the sheath by weight.

16. The method of claim 1, wherein the plasticizer content of the first gel-forming composition comprises about 10% to about 50% by weight.

17. The method of claim 1, wherein the plasticizer content of the second gel-forming composition comprises about 1% to about 10% by weight.

18. The method of claim 1, wherein the plasticizer comprises a polyol.

19. The method of claim 18, wherein the polyol comprises glycerol, sorbitol, maltitol, xylitol, or combinations thereof.

20. The method of claim 1, wherein the first gel-forming composition further comprises an active ingredient.

21. The method of claim 20, wherein, wherein the active ingredient is selected from the group consisting of NTHEs, analgesics, antihistaminics, anti-asthmatics, anti-epileptics, antibiotics, decongestants, anti-allergenics, and food supplements.

* * * * *